United States Patent [19]

Buzzetti et al.

[11] Patent Number: 4,840,943
[45] Date of Patent: Jun. 20, 1989

[54] ANDROST-4-ENE-3,17-DIONES AND PROCESS FOR THEIR PREPARATION

[75] Inventors: Franco Buzzetti, Monza; Enrico di Salle; Paolo Lombardi, both of Milan, all of Italy

[73] Assignee: Farmitalia Carlo Ebra S.r.l., Milan, Italy

[21] Appl. No.: 61,663

[22] Filed: Jun. 15, 1987

[30] Foreign Application Priority Data

Jun. 20, 1986 [GB] United Kingdom ............... 8615092

[51] Int. Cl.⁴ .................. C07J 53/00; C07J 75/00; C07D 31/705; C07D 31/565
[52] U.S. Cl. .................... 514/177; 260/397.3
[58] Field of Search ................. 260/397.3; 514/177

[56] References Cited

U.S. PATENT DOCUMENTS 2,744,120  5/1956  Fried et al. ............... 260/343.2
4,235,893 11/1980  Brodie et al. ............. 260/397.4

FOREIGN PATENT DOCUMENTS 929985  6/1963  United Kingdom .
1263992  2/1972  United Kingdom .

OTHER PUBLICATIONS

Derwent Abstract 3995S-B for Bel 759,886 (1971).
Derwent Publication for GB 1,042,291.
Derwent Publication for NL 6503784.
Derwent Publication for EP 210 832.
GB 2177-700A Pharmaeuticals p. 3 Week 8704.
Petrow et al Chemical Abstracts, 100:96848q.
Derwent Publication for BE 816363.
Brodie, "Overview of Recent . . . " Cancer Research (Suppl) 42, 3312s–3314s, Aug. (1982).
Covey et al, "A New Hypothesis Based . . . " Cancer Research (Suppl) 42,3327s–3333s Aug. (1982).
Derwent Publication for U.S. Pat. No. 4,289,762.
Derwent Publication for U.S. Pat. No. 4,322,416.
Metcalf, et al "Substrate-Induced . . . " J. Am. Chem. Soc. 1981, 103, 3221–3222.
Derwent Publication for EP100566.
Derwent Publication for GB2100601.
Derwent Publication for U.S. Pat. No. 4,071,625.
Derwent Publication for DE3422187.
Petrow Chemical Abstracts vol. 60 9336a.
Chemical Abstracts U.S. Pat. No. 3,112,305, vol. 60, 9337.
Farmdoc Abstract, SA 65/4327.
Farmdoc Abstract, U.S. Pat. No. 3,356,694.
Korp et al, "Efficient Synthesis and Mechanisms of Formation . . . " J.C.S. Chem. Comm. 1973, pp. 72–73.
Abstract for EP 129,500.
Wiechert, Chem. Abs 105, 24487b (1985).

Primary Examiner—Mark L. Berch
Attorney, Agent, or Firm—Armstrong, Nikaido, Marmelstein, Kubovcik & Murray

[57] ABSTRACT

The present invention relates to new 6-substituted 1.2β methylenandrost-4-ene-3,17-diones of the following general formula:

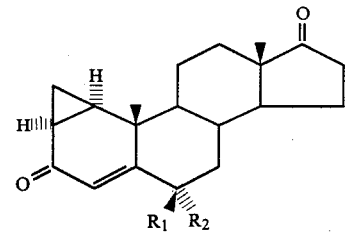

wherein one of $R_1$ and $R_2$ is hydrogen and the other is halogen, amino or azido, or $R_1$ and $R_2$, taken together, form a $=CH_2$ or $=O$ group, and, when one of $R_1$ and $R_2$ is amino, the pharmaceutically acceptable salts thereof.

The compounds of the invention are useful in therapy, in particular as anti-cancer agents.

5 Claims, No Drawings

ANDROST-4-ENE-3,17-DIONES AND PROCESS FOR THEIR PREPARATION

The present invention relates to new 6-substituted 1,2β-methylenandrost-4-ene-3,17-diones, to a process for their preparation, to pharmaceutical compositions containing them, and to the use of said compounds for the treatment of hormone-dependent cancers in mammals. Basic and clinical data indicate that aromatized metabolites of androgens, i.e. the estrogens, are the hormones involved in the pathogenic cellular changes associated with the growth of some hormone-dependent cancers, such as breast, endometrial and ovarian carcinomas.

Estrogens are also involved in the pathogenesis of benign prostatic hyperplasia.

Endogenous estrogens are ultimately formed from either androstenedione or testosterone as immediate precursors.

The reaction of central importance is the aromatization of the steroidic ring A, which is performed by the enzyme aromatase. As aromatization is a unique reaction and the last in the series of steps in the biosynthesis of estrogens, it has been envisaged that an effective inhibition of the aromatase, resulting from compounds able to interact with the aromatizing steps, may have useful application for controlling the amount of circulating estrogens, estrogen-dependent processes in reproduction, and estrogen-dependent tumours. Known steroidal substances which have been reported to be endowed with an aromatase-inhibiting action are, for example, Δ¹-testololactone [U.S. Pat. 2,744,120], 4-hydroxy-androst-4-ene-3,17-dione and esters thereof [see, for example, U.S. Pat. No. 4,235,893], 10-(1,2-propadienyl)-estr-4-en-3,17-dione [U.S. Pat. No. 4,289,762], 10-(2-propynyl)-estr-4-ene-3,7-dione [J. Am. Chem. Soc., 103, 3221 (1981) and U.S. Pat. No. 4,322,416], 19-thioandrostene derivatives (Europ. Pat. Appl. 100566), androsta-4,6-diene-3,17-dione, androsta-1,4,6-triene-3,17-dione [G.B. Pat. Appl. 2,100,601A] and androsta-1,4-diene-3,17-dione [Cancer Res. (Suppl.) 42, 3327 (1982)]. The present invention provides compounds having the following general formula (I)

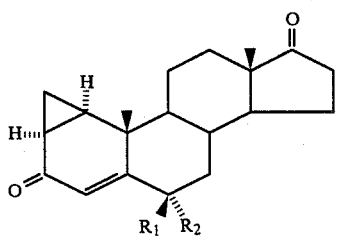

(I)

wherein
one of $R_1$ and $R_2$ is hydrogen and the other is halogen, amino or azido, or $R_1$ and $R_2$, taken together, form a $=CH_2$ or $=O$ group, and, when one of $R_1$ and $R_2$ is amino, the pharmaceutically acceptable salts thereof.

The invention also includes within its scope all the possible isomers, stereoisomers and their mixtures, and the metabolite and the metabolic precursors or bioprecursors of the compounds of formula (I).

In the formulae of this specification the broken lines ( ॥॥॥॥ ) indicate that the substituents are in the α-configuration, i.e. below the plane of the ring, while the heavy solid lines (⌇⌇⌇) indicate that the substituents are in the β-configuration, i.e. above the plane of the ring; a wavy bond (━━) indicates that a substituent may be either in the α-configuration or in the β-configuration or both.

A halogen atom is e.g. fluorine, chlorine or bromine, in particular fluorine or bromine, more preferably fluorine.

Examples of pharmaceutically acceptable salts are either those with inorganic acids, e.g. hydrochloric, hydrobromic, nitric and sulphuric acids and with organic acids, e.g. citric, tartaric, maleic, malic, fumaric, methanesulphonic and ethanesulphonic acids. As stated above, the present invention also includes within its scope pharmaceutically acceptable bioprecursors (otherwise known as pro-drugs) of the compounds of formula (I), i.e. compounds which have a different formula to formula (I) above but which nevertheless upon administration to a human being are converted directly or indirectly in vivo into a compound of formula (I).

Preferred compounds of the invention are the compounds of formula (I), wherein:
one of $R_1$ and $R_2$ is hydrogen and the other is fluorine, bromine or amino, or $R_1$ and $R_2$ taken together form a $=CH_2$ group and, when one of $R_1$ and $R_2$ is amino, the pharmaceutically acceptable salts thereof.

Examples of specific compounds of the invention are:
6-methylen-1,2β-methylenandrost-4-ene-3,17-dione
6β-fluoro-1,2β-methylenandrost-4-ene-3,17-dione
6α-fluoro-1,2β-methylenandrost-4-ene-3,17-dione
6β-chloro-1,2β-methylenandrost-4-ene-3,17-dione
6α-chloro-1,2β-methylenandrost-4-ene-3,17-dione
6β-bromo-1,2β-methylenandrost-4-ene-3,17-dione
6α-bromo-1,2β-methylenandrost-4-ene-3,17-dione
6β-amino-1,2β-methylenandrost-4-ene-3,17-dione
6α-amino-1,2β-methylenandrost-4-ene-3,17-dione
6β-azido-1,2β-methylenandrost-4-ene-3,17-dione
6α-azido-1,2β-methylenandrost-4-ene-3,17-dione; and
1,2β-methylenandrost-4-ene-3,6,17-trione; and the pharmaceutically acceptable salts of the 6-amino derivatives hereabove mentioned.

The compounds of the invention and the pharmaceutically acceptable salt thereof can be obtained by a process comprising:
(a) methylenating a compound of formula (II)

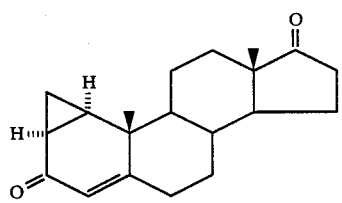

(II)

thus obtaining a compound of formula (I) wherein $R_1$ and $R_2$, taken together, form a $=CH_2$ group; or
(b) oxygenating a compound of formula (II), as defined above, thus obtaining a compound of formula (I) wherein $R_1$ and $R_2$, taken together, form an $=O$ group; or
(c) halogenating a compound of formula (II), as defined above, thus obtaining a compound of formula (I), wherein $R_1$ is halogen and $R_2$ is hydrogen; or
(d) isomerizing a compound of formula (I), wherein $R_1$ is halogen and $R_2$ is hydrogen, thus obtaining another compound of formula (I), wherein $R_1$ is hydrogen and $R_2$ is halogen; or (e) converting a compound of formula (I), wherein one of $R_1$ and $R_2$ is halogen and the other is hydrogen, into the corresponding compound of formula (I), wherein one of $R_1$ and $R_2$ is azido and the other is hydrogen; or (f) converting a compound of formula (I), wherein one of $R_1$ and $R_2$ is azido and the other is hydrogen, into the corresponding compound of formula (I), wherein one of $R_1$ and $R_2$ is amino and the other is hydrogen; or (g) converting a compound of formula (I), wherein one of $R_1$ and $R_2$ is bromine and the other is hydrogen, into the corresponding compound of formula (I), wherein one of $R_1$ and $R_2$ is fluorine and the other is hydrogen; and, if desired, converting a compound of formula (I) into another compound of formula (I), and/or, if desired, separating a mixture of isomers of compounds of formula (I) into the single isomers, and/or, if desired, salifying a compound of formula (I) wherein one of $R_1$ and $R_2$ is amino, and/or, if desired, obtaining a free base of formula (I) from a salt thereof.

Methylenation, i.e. 6-methylenation, of a compound of formula (II) may be carried out according to known methods, e.g. according to K. Annen et al., Synthesis 1982, 34. Preferably a compound of formula (II) is reacted with formaldehyde diethylacetal in a suitable organic solvent, e.g. chloroform, at reflux temperature, in the presence of a condensing agent, e.g. phosphoryl chloride and sodium acetate. Alternatively, the same reaction may be carried out in other inert organic solvents, e.g. 1,2-dichloroethane, diethylether or dioxane and in the presence of other suitable condensing agents, e.g. phosphorous pentoxide or p-toluenesulfonic acid.

Oxygenation, i.e. 6-oxygenation, of a compound of formula (II) may be carried out according to known methods, e.g. by bubbling air or oxygen in the presence of a suitable basic agent. Preferably the reaction is performed according to B. Camerino, Gazz. Chim. Ital., 92, 693 (1962). In particular the compound of formula (II) is reacted with oxygen in a lower alcohol solution, e.g. in t-butanol, in the presence of a basic agent, e.g. potassium t-butoxide, at a temperature ranging from about 20° C. to about 60° C. and for reaction times ranging from about 2 hours to about 48 hours.

Halogenation of a compound of formula (II), i.e. 6β-halogenation, may be carried out according to known procedures, for example, by reaction with a suitable N-haloacylamide, e.g. N-bromosuccinimide or N-chlorosuccinimide, in an inert organic solvent, e.g. carbon tetrachloride, at a temperature ranging from about room temperature to reflux temperature.

Isomerization of a compound of formula (II), wherein $R_1$ is halogen and $R_2$ is hydrogen may be performed by following well known procedures, e.g. through a suitable isomerizing agent or by heating to high temperatures, e.g. up to about 200° C. Preferably the isomerization is carried out by treatment with a hydrohalic acid, e.g. hydrochloric acid, in an organic solvent which may be e.g. a lower alcohol, preferably ethanol, or acetic acid, at temperatures ranging from about 20° C. to about 100° C.

The conversion of a compound of formula (I), wheren $R_1$ is halogen and $R_2$ is hydrogen, into another compound of formula (I), wherein $R_2$ is azido and $R_1$ is hydrogen, or alternatively the conversion of a compound of formula (I), wherein $R_1$ is hydrogen and $R_2$ is halogen, into another compound of formula (I), wherein $R_2$ is hydrogen and $R_1$ is azido may be performed by following known procedures. For example a 6β-bromo or, respectively, 6α-bromo derivative may be reacted with sodium azide in a dipolar aprotic solvent, such as dimethylformamide or dimethyl sulfoxide, at a temperature ranging from about 0° C. to about 150° C.

The conversion of a compound of formula (I), wherein $R_1$ is azido and $R_2$ is hydrogen, into another compound of formula (I), wherein $R_1$ is amino and $R_2$ is hydrogen, or alternatively the conversion of a compound of formula (I), wherein $R_1$ is hydrogen and $R_2$ is azido, into another compound of formula (I), wherein $R_1$ is hydrogen and $R_2$ is amino, may be carried out according to known reduction procedures. 6β-azido or, respectively, 6α-azido derivative may be selectively reduced e.g. according to H. Bayley et al., Tetrahedron Letters, 3633 (1978), and preferably by treatment with 1,3-propanedithiol in a lower alcohol solution, e.g. methanol solution, at temperatures ranging from about 0° C. to reflux temperature.

The conversion of a compound of formula (I), wherein $R_1$ is bromine and $R_2$ is hydrogen, into another compound of formula (I) wherein $R_1$ is fluorine and $R_2$ is hydrogen or, alternatively, the conversion of a compound of formula (I), wherein $R_1$ is hydrogen and $R_2$ is bromine, into another compound of formula (I), wherein $R_1$ is hydrogen and $R_2$ is fluorine, may be performed according to known methods, e.g. J. Mann et al., J. Chem. Soc. Perkin Trans I, 2681 (1983). For example a 6β-bromo or 6α-bromo derivative may be reacted with pyridinium poly(hydrogen fluoride) in the presence of mercury (II) oxide at a temperature ranging from about 0° C. to about 80° C.

A compound of formula (I) may be converted into another compound of formula (I) according to known methods. The process-variants (e), (f), and (g) described above, for instance, may also be considered as examples of optional conversion of a compound of formula (I) into another compound of formula (I).

Also the optional salification of a compound of formula (I) wherein one of $R_1$ and $R_2$ is amino, as well as the conversion of a salt into the free compound and the separation of a mixture of isomers of compounds of formula (I) into the single isomers may be carried out by conventional methods.

The starting compound of formula (II) is known. For instance, it may be prepared by following the procedure described in Example 24 of U.S. Pat. 4,071,625: according to this procedure the starting material is 1,4-androstadiene-3,17-dione and the last reaction-step involves the oxidation of 1β,2β-methylen-5-androstene-3β,17β-diol dissolved in acetone through Jones reagent.

The compounds of the present invention are inhibitors of the biotransformation of androgens into estrogens, i.e., they are steroidal aromatase inhibitors.

The aromatase inhibitory activity of these compounds was demonstrated by employing the in vitro test described by Thompson and Siiteri (E. A. Thompson and P. K. Siiteri, J. Biol. Chem. 249, 5364, 1974) which utilizes the human placental microsomal fraction as enzyme source. In this test the aromatization rate of androstenedione into estrone was evaluated by incubating [1β,2β-$^3$H]androstenedione (50 nM) in the presence of NADPH with the enzyme preparation and by measuring the amount of $^3$H$_2$O formed during 20 min incubation at 37° C.

The new compounds, incubated at various concentrations, showed a relevant aromatase inhibitory activity.

By virtue of their ability to inhibit aromatase and, consequently, to reduce estrogen levels, the new compounds are useful in the treatment and prevention of various estrogen dependent diseases, i.e., breat, endometrial, ovarian and pancreatic cancers, gynecomastia, benign breast disease, endometriosis, polycystic ovarian disease and precocious puberty. Another application of the compounds of the invention is in the therapeutic and/or prophylactic treatment of prostatic hyperplasia, a disease of the estrogen dependent stromal tissue.

The new compounds can find also use for the treatment of male infertility associated with oligospermia and for female fertility control, by virtue of their ability to inhibit ovulation and egg nidation.

In view of their high therapeutic index, the compounds of the invention can be used safely in medicine. For example, the approximate acute toxicity ($LD_{50}$) of the compounds of the invention in the mouse, determined by single administration of increasing doses and measured on the seventh day after the treatment was found to be negligible.

The compounds of the invention can be administered in a variety of dosage forms, e.g. orally, in the form of tablets, capsules, sugar or film coated tablets, liquid solutions or suspensions; rectally, in the form of suppositories; parenterally, e.g. intramuscularly, or by intravenous injection or infusion.

The dosage depends on the age, weight, conditions of the patient and administration route; for example the dosage adopted for oral administration to adult humans may range from about 10 to about 150–200 mg pro dose, from 1 to 5 times daily.

The invention includes pharmaceutical compositions comprising a compound of the invention in association with a pharmaceutically acceptable excipient (which can be a carrier or diluent). The pharmaceutical compositions containing the compounds of the invention are usually prepared following conventional methods and are administered in a pharmaceutically suitable form.

For example, the solid oral forms may contain, together with the active compound, diluents, e.g., lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. a starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

The liquid dispersions for oral administration may be e.g. syrups, emulsions and suspensions.

The syrups may contain as carrier, for example, saccharose or saccharose with glycerine and/or mannitol and/or sorbitol. The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

The solutions for intravenous injections or infusions may contain as carrier, for example, sterile water or preferably they may be in the form of sterile, aqueous, isotonic saline solutions. The suppositories may contain together with the active compound a pharmaceutically acceptable carrier, e.g. cocoa-butter, polyethylene glycol, a polyoxyethylene sorbitan fatty acid ester surfactant or lecithin.

The following examples illustrate but do not limit the invention.

EXAMPLE 1

A mixture of sodium acetate (1 g), absolute chloroform (30 ml), formaldehyde diethyl acetal (30 ml, 0.24 mol), phosphoryl chloride (3.8 ml, 0.04 mol), and 1,2$\beta$-methylenandrost-4-en-3,17-dione (0.806 g, 2.7 mmol) is stirred at reflux for about 5 hours, i.e. until the starting material has disappeared. The suspension is allowed to cool and under vigorous stirring a saturated sodium carbonate solution is added dropwise until the pH of the aqueous layer becomes alkaline (ca. 1 hour). The organic layer is separated, neutralized with water, and dried with sodium sulfate. After concentration under reduced pressure the oily residue is purified by chromatography on silica gel using hexane/ethyl acetate as eluent. Thus the pure 6-methylen-1,2$\beta$-methylenandrost-4-ene-3,17-dione is obtained in 60% yield (0.194 g).

Found: C 81.10, H 8.35. $C_{21}H_{26}O_2$ requires: C 81.25, H 8.44.

N.M.R. $\delta$ p.p.m.: 0.92 (3H, s); 1.18 (3H, s); 4.82 (2H, m); 5.60 (1H, s) MS (m/Z): 310.

EXAMPLE 2

To a solution of 1,2$\beta$-methylenandrost-4-ene-3,17-dione (0.2 g) in tert-butanol (5 ml) potassium tert-butoxide (0.26 g) is added and the mixture stirred vigorously for 24 hours at room temperature. Then ice water and diethyl ether are added, the ethereal extract washed with water, dried, and concentrated under reduced pressure. The residue is chromatographed on silica gel using n-hexane/ethyl acetate to give 0.15 g of 1,2$\beta$-methylenandrost-4-ene-3,6,17-trione. Found: C 81.01, H 8.05. $C_{20}H_{24}O_2$ requires: C 81.04, H 8.16.

EXAMPLE 3

A mixture of 1,2$\beta$-methylenandrost-4-ene-3,17-dione (2.44 g), N-bromosuccinimide (2.33 g), benzoyl peroxide (0.060 g), and carbon tetrachloride (200 ml) are heated to reflux for 4 hours. After cooling to room temperature the precipitate is filtered off, the residue washed with carbon tetrachloride and the combined filtrates evaporated in vacuo. The residue is chromatographed on silica gel using benzene/ethyl ether to give pure 6$\beta$-bromo-1,2$\beta$-methylenandrost-4-ene-3,17-dione (2.16 g, 70%).

Found: C 63.40, H 6.58, Br 21.05. $C_{20}H_{25}BrO_2$ requires: C 63.66, H 6.68, Br 21.18.

N.M.R. $\delta$ p.p.m.: 0.90 (2H, m); 0.98 (3H, s); 1.66 (3H, s); 4.84 (1H, d); 5.79 (1H, s).

Following the above reported procedure but using N-chlorosuccinimide instead of N-bromosuccinimide, the 6$\beta$-chloro-1,2$\beta$-methylenandrost-4-ene-3,17-dione can be prepared.

Found: C 72.15, H 7.45, Cl 10.55. $C_{20}H_{25}ClO_2$ requires: C 72.17, H 7.57, Cl 10.65.

EXAMPLE 4

6β-Bromo-1,2β-methylenandrost-4-ene-3,17-dione (200 mg) in acetic acid (15 ml) at 15°–20° is treated with a steady stream of dry hydrogen chloride for 1 hour and then kept an additional hour at room temperature. Then water is added and the product isolated with ether. The combined ether extracts are washed with saturated salt solution, 5% sodium carbonate solution, water; dried and evaporated. Column chromatography of residue over silica gel using benzene/ethyl ether as eluant affords pure 6α-bromo-1,2β-methylenandrost-4-ene-3,17-dione (150 mg, 75%).

Following the above reported procedure and starting from the 6β-chloro-1,2β-methylenandrost-4-ene-3,17-dione the epimeric 6α-chloro-1,2β-methylenandrost-4-ene-3,17-dione can be prepared.

EXAMPLE 5

6β-Bromo-1,2β-methylenandrost-4-ene-3,17-dione (0.72 g, 1.9 mmol) is added to a vigorously stirred suspension of yellow mercury (II) oxide (0.83 g, 3.8 mmol) in pyridinium poly (hydrogen fluoride) (7 ml) at room temperature. After 3 hours the mixture is poured onto crushed ice and extracted with dichloromethane. The combined extracts are washed with water, dried and evaporated in vacuo. The residue is chromatographed twice on silica gel using benzene/ethyl ether as eluant to yield pure 6β-fluoro-1,2β-methylenandrost-4-ene-3,17-dione (0.300 g, 50%).

Found: C 75.85, H 7.91, F 5.91. $C_{20}H_{25}FO_2$ requires: C 75.92, H 7.96, F 6.00.

Starting from 6α-bromo-1,2β-methylenandrost-4-ene-3,17-dione and using the above reported procedure the 6α-fluoro-1,2β-methylenandrost-4-ene-3,17-dione can be obtained.

EXAMPLE 6

A mixture of 6β-bromo-1,2β-methylenandrost-4-ene-3,17-dione (378 mg, 1 mmol), sodium azide (66 mg, 1 mmol) and dimethylformamide (10 ml) is heated from 20° to 100° C. Then the reaction mixture is cooled, poured onto ice water and extracted with ethyl acetate. The organic layer is separated, washed with water, dried and evaporated in vacuo. Purification is achieved by column chromatography over silica gel eluting with benzene/ether to yield pure 6α-azido-1,2β-methylenandrost-4-ene-3,17-dione (238 mg, 70%). Found: C 70.61, H 7.35, N 12.27. $C_{20}H_{25}N_3O_2$ requires: C 70.77, H 7.12, N, 12.38.

Following the same procedure but starting from the 6α-bromo-1,2β-methylenandrost-4-ene-3,17-dione the epimeric 6β-azido-1,2β-methylenandrost-4-ene-3,17-dione can be synthesized.

EXAMPLE 7

A mixture of 6α-azido-1,2β-methylenandrost-4-ene-3,17-dione (1695 mg, 5 mmol), 1,3-propanedithiol (0.25 ml, 2.5 mmol), triethylamine (0.35 ml, 2.5 mmol) and methanol (2.5 ml) is stirred for 6 hours at room temperature. Then the reaction mixture is evaporated in vacuo to dryness. The residue is taken up in ether, the etheral solution washed with water, dried and evaporated in vacuo. Column chromatography of the residue over silica gel affords the pure 6α-amino-1,2β-methylenandrost-4-ene-3,17-dione (1000 mg, 64%).

Found: C 76.59, H 8.57, N 4.39. $C_{20}H_{27}NO_2$ requires: C 76.64, H 8.68, N 4.47.

Starting from 6β-azido-1,2β-methylenandrost-4-ene-3,17-dione and following the above reported procedure the 6β-amino-1,2β-methylenandrost-4-ene-3,17-dione can be prepared.

EXAMPLE 8

To a solution of 6α-amino-1,2β-methylenandrost-4-ene-3,17-dione (200 mg) in isopropyl ether (10 ml) a stoichiometric amount of HCl is added, thus obtaining 6α-amino-1,2β-methylenandrost-4-ene-3,17-dione hydrochloride, which is filtered off, washed with isopropyl ether and dried.

EXAMPLE 9

Tablets each weighing 0.150 g and containing 25 mg of the active substance, can be manufactured as follows:
Composition (for 10,000 tablets):
6-methylen-1,2β-methylenandrost-4-ene-3,17-dione: 250 g
Lactose: 800 g
Corn starch: 415 g
Talc powder: 30 g
Magnesium stearate: 5 g The 6-methylen-1,2β-methylenandrost-4-ene-3,17-dione, the lactose and half the corn starch are mixed; the mixture is then forced through a sieve of 0.5 mm mesh size. Corn starch (10 g) is suspended in warm water (90 ml) and the resulting paste is used to granulate the powder.

The granulate is dried, comminuted on a sieve of 1.4 mm mesh size, then the remaining quantity of starch, talc and magnesium stearate is added, carefully mixed and processed into tablets.

EXAMPLE 10

Capsules, each dosed at 0.200 g and containing 20 mg of the active substance can be prepared.
Composition for 500 capsules:
6-methylen-1,2β-methylenandrost-4-ene-3,17-dione: 10 g
Lactose: 80 g
Corn starch: 5 g
Magnesium stearate: 5 g This formulation is encapsulated in two-piece hard gelatin capsules and dosed at 0.200 g for each capsule.

We claim:

1. A compound having the formula (I)

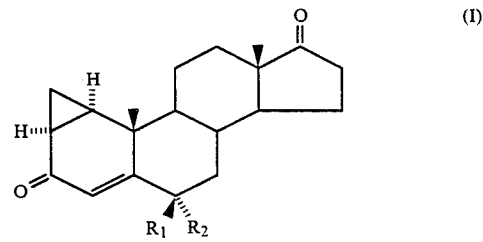

wherein
one of $R_1$ and $R_2$ is hydrogen and the other is amino or azido, or $R_1$ and $R_2$, taken together, form a =$CH_2$ or =O group, and, when one of $R_1$ and $R_2$ is amino, the pharmaceutically acceptable salts thereof.

2. A compound of formula (I), according to claim 1, wherein one of $R_1$ and $R_2$ is hydrogen and the other is amino, or $R_1$ and $R_2$ taken together form a $=CH_2$ group and, when one of $R_1$ and $R_2$ is amino, the pharmaceutically acceptable salts thereof.

3. 6-methylene-1,2β-Methyleneandrost-4-ene-3,17-dione.

4. A compound selected from the group consisting of:
6β-amino-1,2β-methyleneandrost-4-ene-3,17-dione
6α-amino-1,2β-methyleneandrost-4-ene-3,17-dione
6β-azido-1,2β-methyleneandrost-4-ene-3,17-dione
6α-azido-1,2β-methyleneandrost-4-ene-3,17-dione; and
1,2β-methyleneandrost-4-ene-3,6,17-trione; and the pharmaceutically acceptable salts of the 6-amino derivatives hereabove mentioned.

5. A pharmaceutical composition for inhibiting the biotransformation of androgens into estrogens which comprises an amount of a compound according to claim 1 effective to inhibit the biotransformation of an androgen into an estrogen, or a pharmaceutically acceptable salt thereof, together with a pharmaceutically acceptable carrier or diluent.

* * * * *